(12) United States Patent
Arlet

(10) Patent No.: US 9,901,461 B2
(45) Date of Patent: Feb. 27, 2018

(54) SPINAL IMPLANT SYSTEM AND METHOD OF USE

(71) Applicant: Warsaw Orthopedic, Inc., Warsaw, IN (US)

(72) Inventor: Vincent M. Arlet, Philadelphia, PA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/692,463

(22) Filed: Apr. 21, 2015

(65) Prior Publication Data

US 2016/0310289 A1 Oct. 27, 2016

(51) Int. Cl.
*A61F 2/44* (2006.01)
*A61B 17/80* (2006.01)
*A61B 17/70* (2006.01)
*A61F 2/30* (2006.01)
*A61B 17/00* (2006.01)

(52) U.S. Cl.
CPC .......... *A61F 2/447* (2013.01); *A61B 17/7059* (2013.01); *A61B 17/8047* (2013.01); *A61B 17/7035* (2013.01); *A61B 2017/00004* (2013.01); *A61F 2002/30904* (2013.01)

(58) Field of Classification Search
CPC ........ A61F 2/44–2/447; A61B 17/70–17/7098
USPC ............................................. 623/17.11–17.16
See application file for complete search history.

(56) References Cited

U.S. PATENT DOCUMENTS 5,520,690 A * 5/1996 Errico ................ A61B 17/7037
606/287
5,531,746 A 7/1996 Errico et al.
2008/0200984 A1 * 8/2008 Jodaitis ................... A61F 2/442
623/17.16
2008/0249625 A1 * 10/2008 Waugh ................. A61F 2/4465
623/17.16
2010/0106249 A1 * 4/2010 Tyber ..................... A61F 2/447
623/17.11

(Continued)

FOREIGN PATENT DOCUMENTS

WO 2016171906 A1 10/2016

OTHER PUBLICATIONS

WO2016171906 International Search Report prepared by Korean Intellectual Property Office, Government Complex Daejeon Building 4, 189, Cheongsa-ro, Seo-gu, Daejeon, 35208, Republic of Korea, dated Jul. 25, 2016.

(Continued)

*Primary Examiner* — Nicholas Plionis

(57) ABSTRACT

A method for treating a spine is provided. The method includes the steps of: disposing an interbody implant adjacent a first vertebral surface and a second vertebral surface of an intervertebral disc space, the interbody implant engaging the vertebral surfaces at a selected angular orientation; connecting the interbody implant with at least one of the vertebral surfaces via at least one fastener that is engaged with the interbody implant and fixed with the vertebral surface such that the at least one fastener is movable to a plurality of axial orientations relative to the interbody implant; and manipulating the vertebral surfaces such that the at least one fastener is fixed relative to the interbody implant. Spinal implants, surgical instruments and systems are disclosed.

20 Claims, 14 Drawing Sheets

(56) References Cited

U.S. PATENT DOCUMENTS

2010/0145460 A1    6/2010  McDonough et al.
2013/0238095 A1*  9/2013  Pavento ............. A61B 17/7059
                                                          623/17.16

OTHER PUBLICATIONS

WO2016171906 Written Opinion of the International Search Authority prepared by Korean Intellectual Property Office, dated Jul. 21, 2016.

* cited by examiner

SPINAL IMPLANT SYSTEM AND METHOD OF USE

TECHNICAL FIELD

The present disclosure generally relates to medical devices for the treatment of musculoskeletal disorders, and more particularly to a surgical system and method for treating a spine.

BACKGROUND

Spinal pathologies and disorders such as degenerative, isthmic and iatrogenic spondylolisthesis, degenerative disc disease, disc herniation, and stenosis may result from disease and degenerative conditions caused by injury, prior surgery and aging. These spinal disorders typically result in symptoms including deformity, pain, nerve damage, and partial or complete loss of mobility. Kyphosis and lysthesis or anterior translation of one vertebra in relation to the next may occur in many of these conditions and pathologies.

Non-surgical treatments, such as medication, rehabilitation and exercise can be effective, however, may fail to relieve the symptoms associated with these disorders. Current surgical treatment of these spinal disorders includes decompression and restoration of the normal alignment of the spine with concomitant fusion. Techniques used to commonly achieve these goals may include laminectomy, discectomy, internal spinal fixation, correction of the kyphotic deformity and the insertion of implantable interbody prosthetics. As part of these surgical treatments, spinal constructs, such as, for example, bone fasteners, spinal rods and interbody devices can be used to correct the pre-existing kyphosis and vertebral translational deformity and to provide stability to a treated region. For example, during surgical treatment, interbody implants and spinal pedicle screws can be used to correct abnormal alignment of the spinal vertebrae and provide stability serving to immobilize the spinal motion segment, and with bone graft, can result in a stable fusion. This disclosure describes an improvement over these prior technologies.

SUMMARY

In one embodiment, a method for treating a spine is provided. The method comprises the steps of: disposing an interbody implant adjacent a first vertebral surface and a second vertebral surface of an intervertebral disc space, the interbody implant engaging the vertebral surfaces at a selected angular orientation; connecting the interbody implant with at least one of the vertebral surfaces via at least one fastener that is engaged with the interbody implant and fixed with the vertebral surface such that the at least one fastener is movable to a plurality of axial orientations relative to the interbody implant; and manipulating the vertebral surfaces such that the at least one fastener is fixed relative to the interbody implant. In some embodiments, spinal implants, surgical instruments and systems are provided.

BRIEF DESCRIPTION OF THE DRAWINGS

The present disclosure will become more readily apparent from the specific description accompanied by the following drawings, in which.

DETAILED DESCRIPTION

Figure 1:
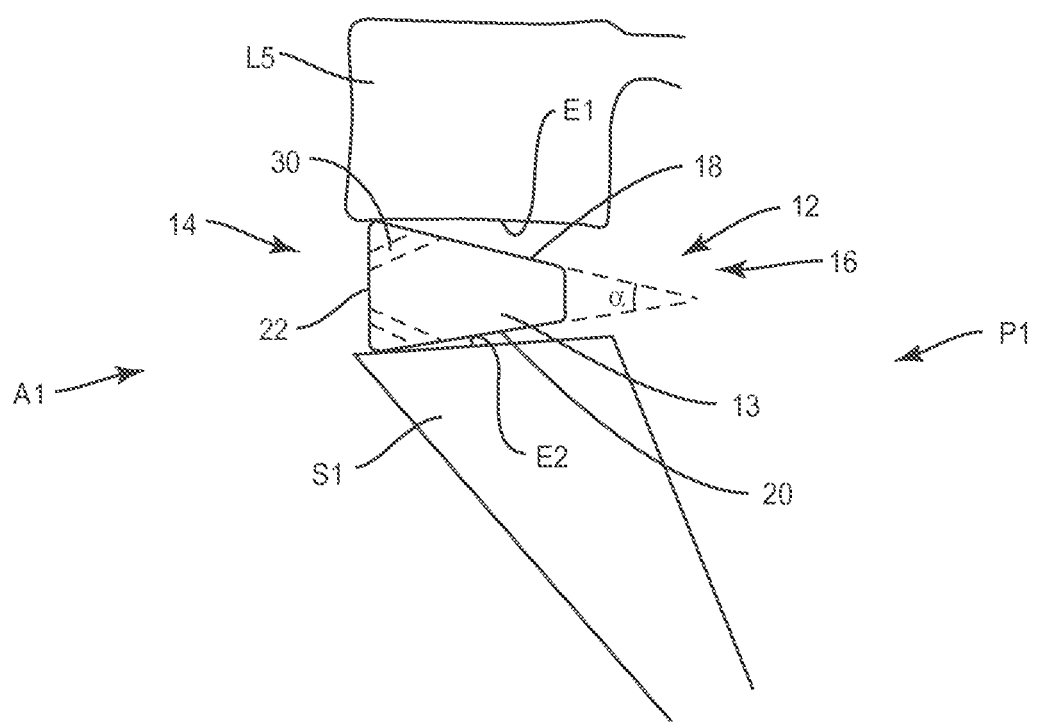
FIG. 1 is a side view of components of one embodiment of a system in accordance with the principles of the present disclosure disposed with vertebrae.

The exemplary embodiments of the surgical system and related methods of use disclosed are discussed in terms of medical devices for the treatment of musculoskeletal disorders and more particularly, in terms of a surgical system including a spinal implant with variable angle screw fixation. In one embodiment, the systems and methods of the present disclosure are employed with a spinal joint fusion, for example, with a cervical region, a thoracic region, a lumbar region, and/or a sacral region of a spine. In some embodiments, the present surgical system comprises a spinal implant including a hyper-lordotic cage with variable angle screw fixation. In some embodiments, the present surgical system includes a spinal implant configured to facilitate curvature and compress a spine posteriorly without a complete pedicle-subtraction osteotomy (PSO). In some embodiments, the present surgical system is employed with a method including a Smith-Petersen osteotomy for removal of posterior-most bony structures.

In some embodiments, the present surgical system comprises a spinal implant including anti-back out screws. In some embodiments, the screws include multiple degrees of freedom and/or play, such as, for example, poly-axial and/or multi-axial screws when engaged with the spinal implant. In some embodiments, the screws are locked and prevented from back out by posterior compression of the spine.

In some embodiments, the present surgical system comprises a spinal implant including a hyper-lordotic wedged cage configured to restore a selected lordotic curve to the spine. In some embodiments, the cage includes apertures configured for engagement with anti-back out screws through the cage. In some embodiments, the screws are non-poly-axial at insertion until a posterior force is applied to impart and support the introduction of lordosis. In some embodiments, the screws are locked into place. In some embodiments, the screws are locked, such as, for example, with slots disposed in the cage. In some embodiments, the screws include heads that slide into the slots when lordosis is imparted and threads on the proximal end of the screws engage and/or penetrate threads or ridges around a proximal periphery of the screw holes. In some embodiments, the cage includes multi-part screw heads configured to prevent back out when a lordotic force is applied. In some embodiments, the cage is configured for disposal of bone graft or osteoinductive material.

In some embodiments, the present surgical system comprises a spinal implant including a cage configured for direct lateral interbody fusion (DLIF) procedures. In some embodiments, the present surgical system utilizes two screws. In some embodiments, the present surgical system utilizes three to four or more screws. In some embodiments, the present surgical system includes a cage configured for anterior lumbar interbody fusion (ALIF) procedures. In some embodiments, the present surgical system is employed with a method to achieve a selected average lordosis for a L5/S1 disc space in a range of 4 through 35 degrees. In some embodiments, the present surgical system is employed with a method to achieve a selected average lordosis for a L5/S1 disc space of 15 degrees. In some embodiments, the present surgical system is employed with a method to achieve a selected average lordosis for a L5 vertebral body in a range of 0 through 19 degrees. In some embodiments, the present surgical system is employed with a method to achieve a selected average lordosis for a L5 vertebral body of 9 degrees. In some embodiments, the present surgical system is employed with a method to achieve a selected average lordosis for a L4/L5 disc space in a range of −2 through 26 degrees. In some embodiments, the present surgical system is employed with a method to achieve a selected average lordosis for a L4/L5 disc space of 12 degrees. In some embodiments, the present surgical system is employed with a method to achieve a selected average lordosis for a vertebral body in a range of 4 through −14 degrees. In some embodiments, the present surgical system is employed with a method to achieve a selected average lordosis for a vertebral body of 3 degrees. In some embodiments, the present surgical system is employed with a method to achieve a selected average lordosis for a L4/L5 disc space of 40 degrees.

In some embodiments, the present surgical system includes a spinal implant configured to prevent plowing into an osteoporotic endplate causing a reduction in an increase of lordosis during posterior correction. In some embodiments, the present surgical system includes a spinal implant configured to prevent backing and/or kicking out of a disc space.

In some embodiments, the present surgical system includes a stabilizing lordotic cage. In some embodiments, the present surgical system is employed with a method to achieve and/or increase lordosis at a lumbo-sacral junction in a range of 25 through 40 degrees. In some embodiments, the cage is configured to prevent back out. In some embodiments, the present surgical system includes pedicle screws employed with a method including spondylolisthesis procedures to correct lordosis during the insertion of a posterior pedicle screw.

In some embodiments, the present surgical system includes a lordotic cage. In some embodiments, the present surgical system includes one or more self-retained, non-locked poly-axial screws. In some embodiments, the screws are locked to the cage and are configured to swivel. In some embodiments, the present surgical system is employed with a method such that the screws include a crown and are configured to prevent back out as the crown of the screw is locked in the cage while allowing angular movement. In some embodiments, the present surgical system is employed with a method such that during posterior surgery and compression, lordosis is increased and the screws do not back out of the cage. In some embodiments, the present surgical system is employed with a method such that during posterior compression, the screws will be disposed in a horizontal orientation and lordosis will increase to prevent back out.

In some embodiments, the present surgical system includes a spinal implant including screws that are locked and fixed. In some embodiments, the present surgical system includes a spinal implant including screws that allow for the correction of lordosis posteriorly. In some embodiments, the present surgical system is employed with a method to achieve and/or increase lordosis to 25 degrees. In some embodiments, the present surgical system is employed with a method to achieve and/or increase lordosis in a range of 25 through 30 degrees. In some embodiments, the present surgical system includes a spinal implant including a poly-axial non-locked screw that comprises two parts. In some embodiments, the spinal implant includes a part having a crown that threads into a metallic portion of a cage such that the crown is locked with the cage. In some embodiments, the spinal implant includes a part having a spherical poly-axial screw head that is retained in the crown and has 25 degrees of freedom of movement in one or a plurality of directions. In some embodiments, the screw is blocked and/or resisted and/or prevented from backing out of the spinal implant when tightened. In some embodiments, a screw driver has a double mechanism, which includes a part for engaging the screw and a part for engaging the crown. In some embodiments, the screw is configured for engagement with a stellar head and an octagonal part.

In some embodiments, the present surgical system includes a poly-axial non-locked or a mono-axial locked screw. In some embodiments, the present surgical system includes a spinal implant that allows use of a locked screw if lordosis is achieved and no further lordosis is desired. In some embodiments, the present surgical system allows the use of a first locked screw and a second poly-axial screw for a moderate increase of lordosis. In some embodiments, for maximum lordosis, both screws are poly-axial in a posterior approach. In some embodiments, a head of the screw is about 7 to about 8 millimeters (mm) in diameter. In some embodiments, a shaft of the screw is about 5 or 6 mm. In some embodiments, the screw is a self-tapping poly-axial screw. In some embodiments, the screw includes a locking thread surface configured to lock with the cage.

In some embodiments, the present surgical system includes a self-retaining non-locked poly-axial screw. In some embodiments, the screw includes a metallic thread configured to lock with the cage. In some embodiments, the screw is self-tapping and self-drilling to lock the poly-axial screw. In some embodiments, the present surgical system includes a screwdriver having two parts or tips, such as, for example, one hexagonal for the screw and one star-like for the crown. In some embodiments, the screwdriver comprises a threaded portion to lock into the crown.

In some embodiments, the present surgical system includes a poly-axial and/or a mono-axial screw utilized to increase lordosis during a posterior approach. In some embodiments, the present surgical system includes caps configured to block and/or lock the screws to prevent backing out. In some embodiments, if no posterior surgery is necessary, mono-axial locking and blocking screws are used.

In some embodiments, the present surgical system includes a cage having an anterior window. In some embodiments, the window allows additional packing of bone graft upon insertion of the cage with tissue. In some embodiments, the present surgical system includes implanting a cage at a L4/L5 vertebral level such that a bottom screw is offset to the left and a top screw is offset to the right. In some embodiments, each screw is slightly offset. In some embodiments, the screws are disposed in a convergent orientation. In some embodiments, a larger screw is inserted into a sacrum S1 and a shorter screw is inserted into a lumbar L5.

In some embodiments, the present surgical system includes a cage having anterior windows disposed adjacent to the screws to pack bone once the cage is inserted with tissue thereby preventing bone graft loss during cage insertion. In some embodiments, bone graft material can be packed into the cage by pushing the bone graft material into the cage through the anterior windows and into the disc space. In some embodiments, the present surgical system is employed with a method including a Smith Petersen osteotomy coupled with insertion of pedicle screws. In some embodiments, the screws are about 30 mm in length and have about a 4.5 to about a 5 mm diameter. In some embodiments, a lordosis of about 25 degrees is achieved.

In some embodiments, the present surgical system includes a cage that includes chambers for bone graft. In some embodiments, the cage includes a plurality of chambers for bone graft. In some embodiments, an outer surface of the cage is knurled and/or spiked. In some embodiments, the cage comprises a chamber for mobility of the screw, such as, for example, posterior mobility. In some embodiments, a poly-axial screw is inserted into the chamber. In some embodiments, the cage is about 26 mm in length and about 30 to about 38 mm wide. In some embodiments, the chambers are about 8 mm to about 9 mm wide. In some embodiments, the chamber for the screw is about 6 mm. In some embodiments, the outer surface of the cage is toothed to prevent kick out. In some embodiments, several poly-axial screws are provided with the cage. In some embodiments, four poly-axial screws are used with the cage for the L5/S1 vertebral level. In some embodiments, the cage includes screws that are laterally inserted with tissue. In some embodiments, four screws are used with the cage for a posterior approach. In some embodiments, four screws are used with an intervertebral body implant. In some embodiments, in the lumbar L4/5 vertebral levels and other vertebral levels including cervical, thoracic and lumbar vertebral levels, smaller poly-axial screws are provided. In some embodiments, the screw holes of the cage can be inserted laterally to avoid the dissection of a bifurcation to the right. In some embodiments, mono-axial or poly-axial screws can be inserted depending on the desire to increase lordosis.

In some embodiments, the present surgical system is employed with a method that includes a cervical spine application. In some embodiments, the present surgical system includes a cervical implant with a threaded step bolt screw mechanism in the middle of the implant. In some embodiments, the present surgical system includes a cervical implant with multiple poly-axial screws. In some embodiments, the cervical implant includes a threaded mechanism for a step bolt screw.

In some embodiments, the cervical spine application comprises poly-axial screws and a threaded step bolt screw mechanism, which increases lordosis with an anterior plate system. In some embodiments, the present surgical system includes a cervical cage having a threaded mechanism in the middle of the cervical cage for a step bolt screw to advance and to draw the spine to a cervical plate. In some embodiments, the cervical cage is about 7 mm in length and about 15 mm wide. In some embodiments, the screw is about 3.5 mm wide. In some embodiments, the threaded step bolt screw mechanism has about a 3 mm thread. In some embodiments, a 7 mm spacer is provided for use in the threaded step bolt screw mechanism. In some embodiments, the screw is about 30 mm in length.

In some embodiments, the present surgical system is employed with a method that includes correction of a cervical kyphotic deformity with a stand-alone instrument including a cage and a plate. In some embodiments, the surgical system includes step bolt screws, standard cervical bone screws and anterior plates. In some embodiments, the present surgical system is employed with a method that includes correction of a kyphotic cervical spine into a lordotic cervical spine such that an implant with a lordotic configuration, which includes freely movable but locked poly-axial screws, and step bolt screws are employed.

In some embodiments, the cervical cage has a width of about 17 mm and converges to adapt to the shape of an anterior disc space. In some embodiments, a top and a bottom of the cage is knurled to prevent kick out. In some embodiments, the cage has a lordosis including a 5 degree increment. In some embodiments, a step bolt mechanism is a poly-axial mechanism with 30 degrees of freedom of movement in each direction to allow tolerance in the plate placement and insertion of a step bolt screw from the plate into a threaded bore hole of the plate. In some embodiments, the cervical cage can be used as a stand-alone cage in the cervical spine. In some embodiments, mono-axial locked screws are employed. In some embodiments, poly-axial screws are provided that are non-locked to allow a small subsidence of the cage into the adjacent endplates to promote fusion and prevent kick out of the cage. In some embodiments, the cage is utilized with posterior spine instrumentation to provide additional lordosis.

In some embodiments, the present surgical system includes a narrow cervical plate to facilitate insertion of a poly-axial step bolt mechanism and allows extension for the poly-axial screws of the cage for locking after the reduction of the kyphosis has used the poly-axial properties of the screws. In some embodiments, the plate includes a narrow portion between the vertebrae and a larger portion at the level of the vertebrae to allow for the insertion of two screws per vertebrae. In some embodiments, a locking mechanism or anti kick out mechanism is provided that is configured for each screw to prevent the back out of the screw.

In some embodiments, present system and methods are employed with a lumbar technique. In some embodiments, a patient is positioned in a supine position on an operating room (OR) table with a radiolucent part of the table over the lumbar spine. In some embodiments, a cage is filled with bone graft material and/or bone enhancer. In some embodiments, once the cage has been inserted, the OR table is oriented to increase the lordosis of the lumbar spine. In some embodiments, if an end plate is in contact on c-arm fluoroscopy, a locking screw is inserted. In some embodiments, if the end plate is not in flush contact with tissue, a poly-axial screw is inserted to allow for further lordosis during posterior compression and osteotomy. In some embodiments, once the cage has been inserted, additional bone graft can be inserted through the anterior window to pack the inside of the cage so that bone fills into the disc space. In some embodiments, a posterior approach is utilized with posterior compression of the segment that increases the segmental lordosis. In some embodiments, Smith Petersen osteotomies of a vertebral segment may be employed to achieve lordosis. In some embodiments, frontal rotation of vertebrae is facilitated with non-locked poly-axial screws. In some embodiments, the cage is prevented from backing out with the poly-axial screws.

In some embodiments, the present surgical system includes a spinal implant comprising a 10 degree spacer including a 20 mm height in a front portion and 13 mm height in a back portion to achieve lordosis of 13 degrees. In some embodiments, the present surgical system includes a spinal implant comprising a 28 degree spacer including a 20 mm height in a front portion and 10 mm height in a back portion to achieve lordosis of 14 degrees and there is a gap posteriorly with no bony contact. In some embodiments, compression in the back portion is provided to increase lordosis to 24 degrees.

In some embodiments, the present surgical system includes blocked screws to prevent backing out while maintaining poly-axial freedom of movement. In some embodiments, the present system and methods provided can be utilized at a lumbar L3/L4 level with Smith Petersen osteotomies. In some embodiments, the present system and methods can achieve overall lordosis for three vertebral levels of about 30 degrees to 60 degrees.

In some embodiments, the present surgical system is employed with a method that includes resection of pedicles for further posterior compression to achieve a contact between the bony end plates and the superior and inferior portions of the cage. In some embodiments, the anterior windows in the cages allow for placement of packed additional bone graft material once the cage has been inserted to achieve fusion. In some embodiments, the present surgical system is employed with a method that includes a transforaminal lumbar interbody fusion (TLIF) approach that provides a posterior discectomy and further posterior compression. In some embodiments, the present system and methods provide about 30 degrees of correction.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-10, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL®), ceramics and composites thereof such as calcium phosphate (e.g., SKELITE), thermoplastics such as polyaryletherketone (PAEK) including polyetheretherketone (PEEK), polyetherketoneketone (PEKK) and polyetherketone (PEK), carbon-PEEK composites, PEEK-BaSO$_4$, polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Spinal implant system 10 may be employed, for example, with minimally invasive procedures, including percutaneous techniques, mini-open surgical techniques and/or open surgical techniques to deliver and introduce instrumentation and/or spinal implants, such as, for example, an interbody implant, such as, for example, a interbody cage 12, as shown in FIG. 1, at a surgical site within a body of a patient, which includes, for example, vertebrae V. In some embodiments, spinal implant system 10 can include spinal constructs including one or more bone fasteners, such as, for example, bone screws, spinal rods, tethers, connectors, plates and/or instruments, as described herein. In some embodiments, spinal implant system 10 is employed to achieve consistent, measured lordosis in a spinal segment of vertebrae V to be corrected and fused, and/or resist and/or prevent inducement of kyphosis. In some embodiments, spinal implant system 10 is employed to utilize the strength properties of a vertebral endplate of vertebrae V to resist and/or prevent subsidence and kyphosis.

Interbody cage 12 includes a body 13 that extends between an anterior surface 14 and a posterior surface 16. Anterior surface 14 is configured to face an anterior side of a body and be disposed adjacent an anterior portion of vertebrae, such as, for example, an anterior portion A1 of a lumbar spine, which includes an L5-S1 intervertebral space of vertebrae V. Posterior surface 16 is configured to face a posterior side of a patient body and be disposed adjacent a posterior portion of vertebrae, such as, for example, a posterior portion P1 of the L5-S1 intervertebral space.

Interbody cage 12 includes a vertebral engaging surface 18 and a vertebral engaging surface 20. Surface 18 is substantially planar and configured to engage endplate tissue of a vertebral body, such as, for example, an endplate E1 of an L5 vertebral body, as shown in FIGS. 1 and 5-8. Surface 20 is configured to engage endplate tissue of a vertebral body, such as, for example, an endplate E2 of an S1 vertebral body. In some embodiments, surfaces 18, 20 may include teeth. In some embodiments, surfaces 18, 20 may be rough, textured, porous, semi-porous, dimpled, knurled, toothed, grooved and/or polished such that it facilitates engagement with tissue. In some embodiments, the vertebral tissue may include intervertebral tissue, endplate surfaces and/or cortical bone.

Surface 18 is disposed at a selected angular orientation α relative to surface 20 to form a wedge shaped configuration of interbody cage 12. In some embodiments, this configuration of interbody cage 12 achieves segmental lordosis of one or more vertebra, as described herein. In some embodiments, angle α includes a range of −2 through 26 degrees. In some embodiments, angle α includes 12 degrees. In some embodiments, angle α includes a range of 4 through −14 degrees. In some embodiments, angle α includes 3 degrees. In some embodiments, angle α includes 40 degrees.

Figure 6:
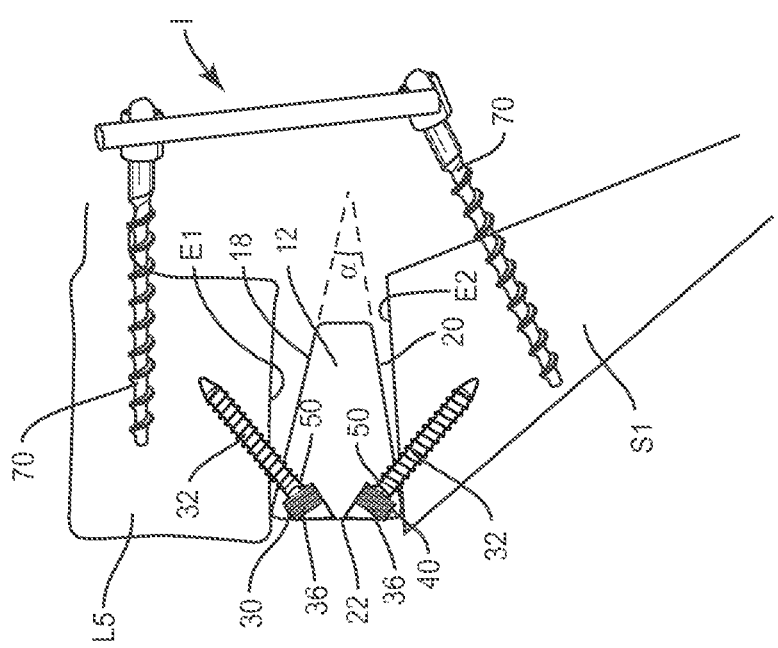
FIG. 6 is a side view of components of one embodiment of a system in accordance with the principles of the present disclosure disposed with vertebrae.
Figure 8:
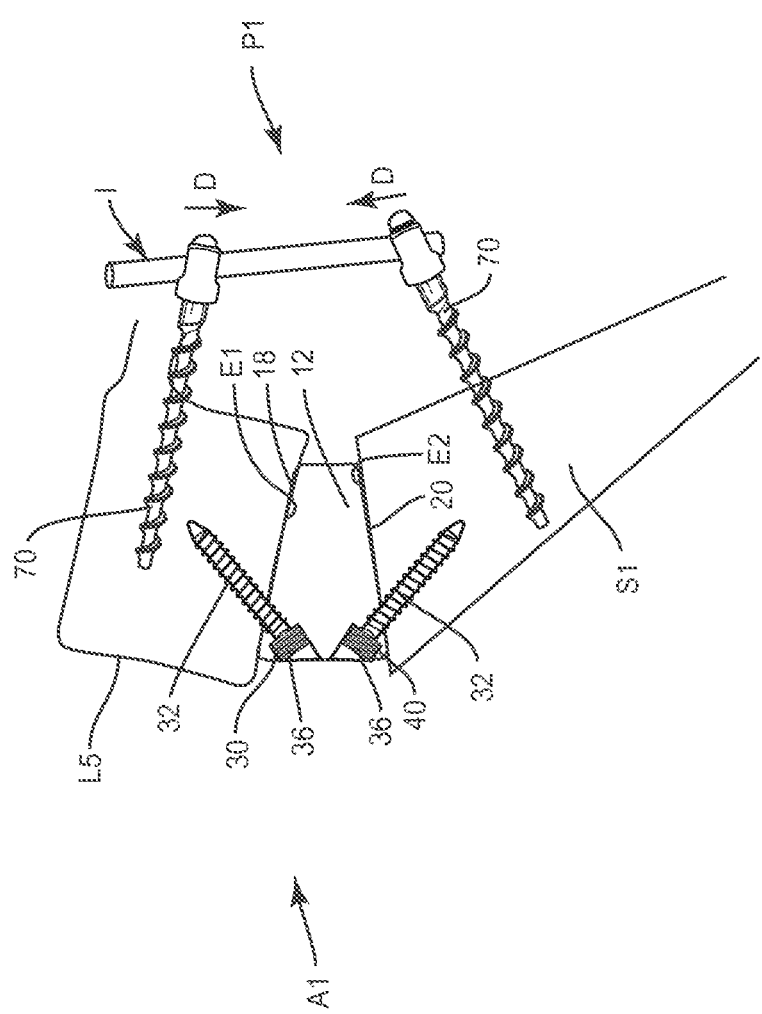
FIG. 8 is a side view of components of one embodiment of a system in accordance with the principles of the present disclosure disposed with vertebrae.

Interbody cage 12 includes a surface 22 disposed anteriorly along interbody cage 12. Surface 22 defines a portion of an opening, such as, for example, an axial slot 30, as shown in FIGS. 1 and 6. Slot 30 extends between surface 22 and surface 18, and includes a portion of surface 18. Slot 30 extends transverse to a longitudinal axis of body 13 and is disposed in alignment with vertebra L5 for fixation with tissue.

Figure 2:
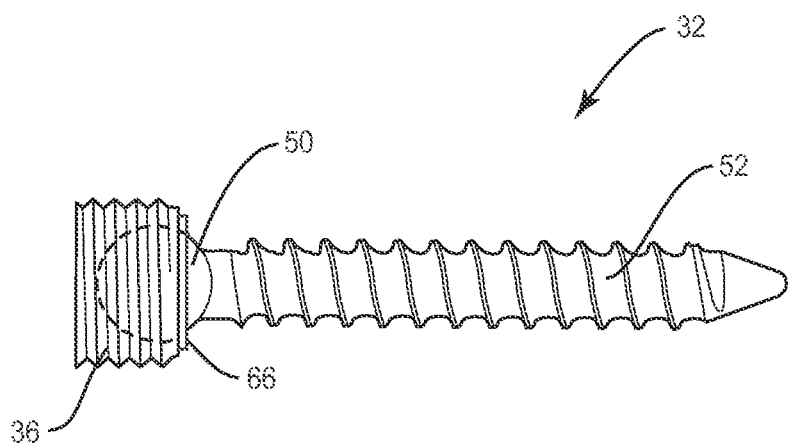
FIG. 2 is a side view of components of one embodiment of a system in accordance with the principles of the present disclosure.

Slot 30 is configured for disposal of a bone fastener, such as, for example, a bone screw 32, as described herein. Spinal implant system 10 includes one or more bone screws 32, as shown in FIG. 2, for attaching interbody cage 12 with tissue, as described herein. Bone screw 32 comprises a portion, such as, for example, a spherical head 50 and a portion, such as, for example, an elongated threaded shaft 52 configured for penetrating tissue. Bone screws 32 are engageable with interbody cage 12 between a first configuration such that bone screws 32 are movable to one or a plurality of axial orientations in angular ranges β1, β2 relative to axes A2, A3, described herein, relative to interbody cage 12 and a second configuration such that bone screws 32 are fixed relative to interbody cage 12.

Figure 3:
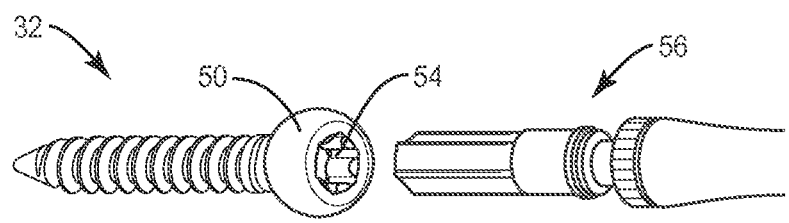
FIG. 3 is a perspective view of components of one embodiment of a system in accordance with the principles of the present disclosure.

Head 50 includes an engagement portion 54 configured for engagement with a surgical instrument 56, as shown in FIG. 3. Shaft 52 has a cylindrical cross section configuration and includes an outer surface having an external thread form. In some embodiments, the external thread form may include a single thread turn or a plurality of discrete threads. In some embodiments, other engaging structures may be located on the shaft, such as, for example, nail configuration, barbs, expanding elements, raised elements and/or spikes to facilitate engagement of the shaft with tissue, such as, for example, vertebrae.

In some embodiments, all or only a portion of shaft 52 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 52 may include one or a plurality of openings. In some embodiments, all or only a portion of the outer surface of shaft 52 may have alternate surface configurations, such as, for example, smooth and/or surface configurations to enhance fixation with tissue, such as, for example, rough, arcuate, undulating, porous, semi-porous, dimpled, polished and/or textured. In some embodiments, all or only a portion of shaft 52 may be cannulated.

Slot 30 extends in a transverse configuration relative to surface 18 and defines an axis A2. In some embodiments, slot 30 facilitates movement of bone screw 32 to one or a plurality of axial orientations in an angular range of β1 relative to axis A2. In some embodiments, bone screw 32 is disposed with slot 30 and engageable with body 13 such that bone screw 32 comprises a multi-axial and/or poly-axial fastener extending from body 13.

In some embodiments, a portion of slot 30 includes a threaded portion 34. Portion 34 is configured for engagement with a member, such as, for example, a crown 36. Crown 36 is configured to support bone screw 32. In some embodiments, bone screw 32 slidably engages and/or translates relative to crown 36 and/or the surface that defines slot 30. In some embodiments, bone screw 32 is movable and/or rotatable to one or a plurality of axial orientations in an angular range of β1 relative to axis A2 and crown 36. In some embodiments, bone screw 32 abuts and/or frictionally engages crown 36 to resist and/or prevent backout of bone screw 32 from tissue and/or body 13.

Figure 5:
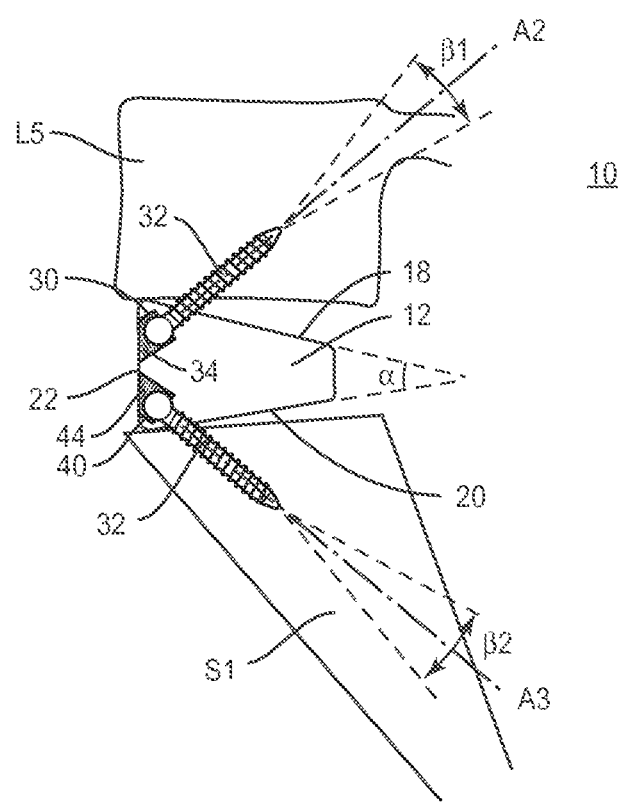
FIG. 5 is a side view of components of one embodiment of a system in accordance with the principles of the present disclosure disposed with vertebrae.
Figure 7:
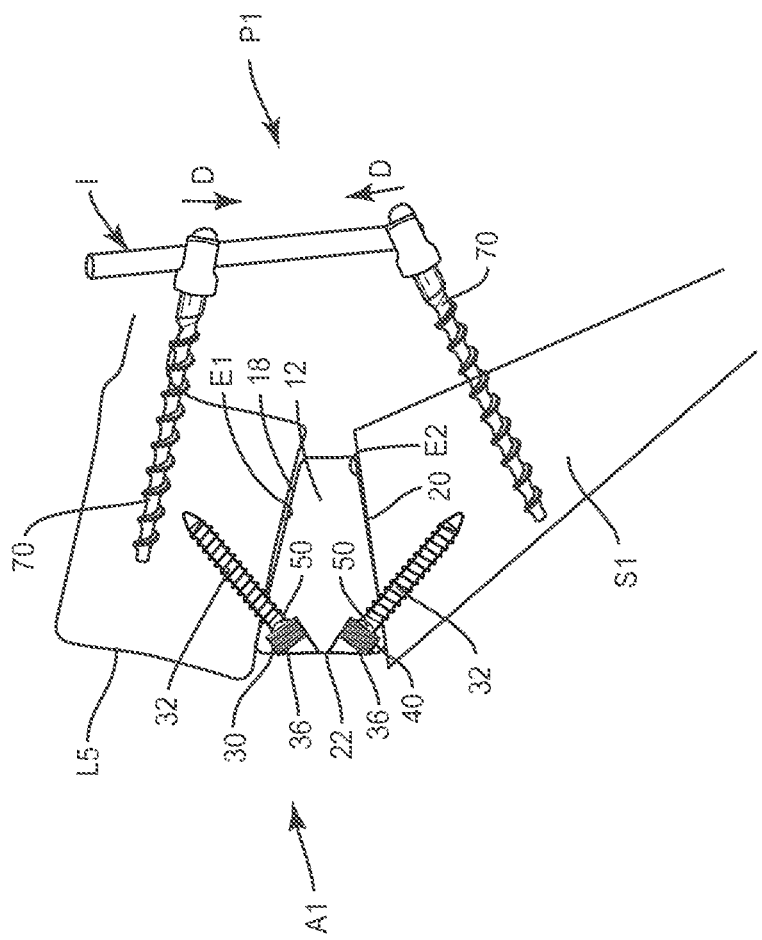
FIG. 7 is a side view of components of one embodiment of a system in accordance with the principles of the present disclosure disposed with vertebrae.

Surface 22 defines a portion of an opening, such as, for example, an axial slot 40, as shown in FIG. 5. Slot 40 extends between surface 22 and surface 20, and includes a portion of surface 20. Slot 40 is disposed in alignment with vertebra S1 for fixation with tissue.

Slot 40 is configured for disposal of a bone screw 32, as described herein. Slot 40 extends in a transverse configuration relative to surface 20 and defines an axis A3. In some embodiments, slot 40 facilitates movement of bone screw 32 to one or a plurality of axial orientations in an angular range of β2 relative to axis A3. In some embodiments, bone screw 32 is disposed with slot 40 and engageable with body 13 such that bone screw 32 comprises a multi-axial and/or poly-axial fastener extending from body 13. In some embodiments, bone screw 32 disposed with slot 40 may be alternately configured relative to a bone screw 32 disposed with slot 30 and/or comprise alternate movement or rotation capabilities relative to a bone screw 32 disposed with slot 30.

In some embodiments, a portion of slot 40 includes a threaded portion 44. Portion 44 is configured for engagement with a crown 36, as described herein. Crown 36 is configured to support a bone screw 32 disposed with slot 40. In some embodiments, bone screw 32 slidably engages and/or translates relative to crown 36 disposed with slot 40 and/or the surface that defines slot 40. In some embodiments, bone screw 32 moves and/or rotates to one or a plurality of axial orientations in an angular range of β2 relative to axis A3 and crown 36 disposed with slot 40. In some embodiments, bone screw 32 abuts and/or frictionally engages crown 36 disposed with slot 40 to resist and/or prevent backout of bone screw 32 disposed with slot 40 from tissue and/or body 13.

Figure 4:
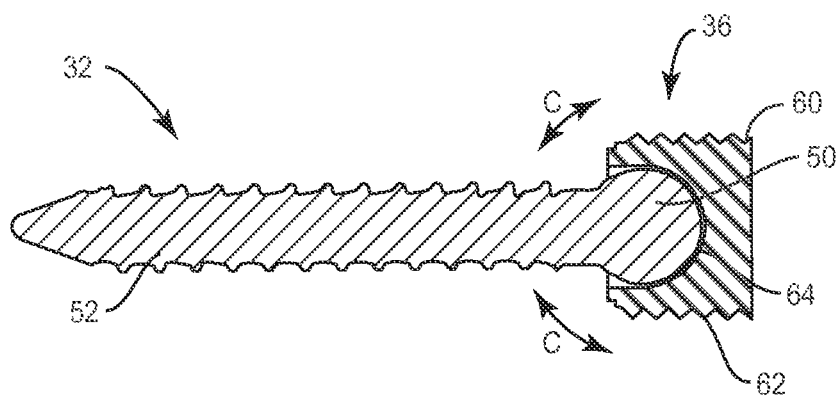
FIG. 4 is a cross section view of components shown in FIG. 2.

Crowns 36 are configured for disposal within slots 30, 40, respectively, and engageable with portions 34, 44. Crown 36 includes a wall 60 having a surface 62 and a surface 64, as shown in FIG. 4. Surface 62 is threaded to facilitate engagement with slots 30, 40. Surface 64 defines a protrusion, such as, for example, a circumferential flange 66. Flange 66 is configured to retain head 50 and facilitate rotation of bone screw 32 forming a self-retained, non-locked multi-axial or poly-axial screw. In some embodiments, bone screw 32 is configured in a locked orientation with crown 36 such that screw 32 is prevented from backing out while maintaining movement within the plurality of axial orientations β1, β2 relative to interbody cage 12. In some embodiments, bone screw 32 is configured in a locked orientation with crown 36 such that screw 32 is prevented from backing out while allowing angular movement and maintaining movement within the plurality of axial orientations β1, β2 relative to interbody cage 12.

In some embodiments, surface 64 is smooth to facilitate rotation of head 50 within crown 36 within the plurality of axial orientations β1, β2 relative to interbody cage 12 in the first configuration, as shown by arrows C in FIG. 4. As bone screw 32 rotates, head 50 engages surface 64 for a friction fit between surface 64 and head 50 into the second configuration to fix bone screw 32 relative to interbody cage 12. In some embodiments, all or only a portion of surface 64 may have alternate surface configurations, such as, for example, rough, arcuate, undulating, porous, semi-porous, dimpled, polished and/or textured to enhance fixation with head 50.

In some embodiments, slot 40 is offset in a lateral direction and slot 30 is offset in a contralateral direction. In some embodiments, slots 30, 40 are slightly offset. In some embodiments, slots 30, 40 are disposed in a convergent orientation.

Figure 10:
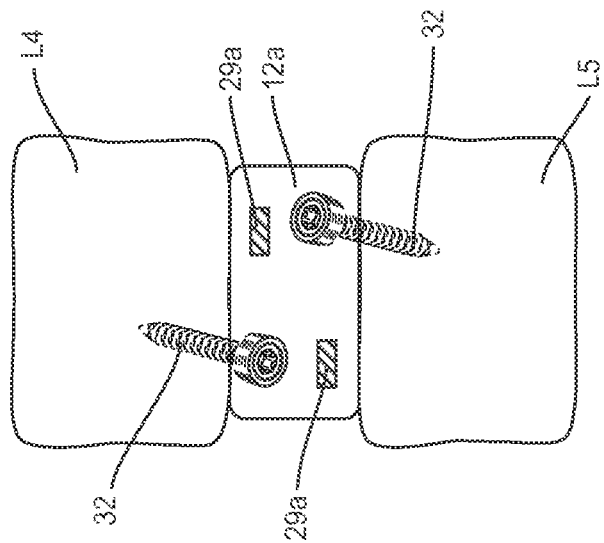
FIG. 10 is a plan view of components of one embodiment of a system in accordance with the principles of the present disclosure disposed with vertebrae.
Figure 9:
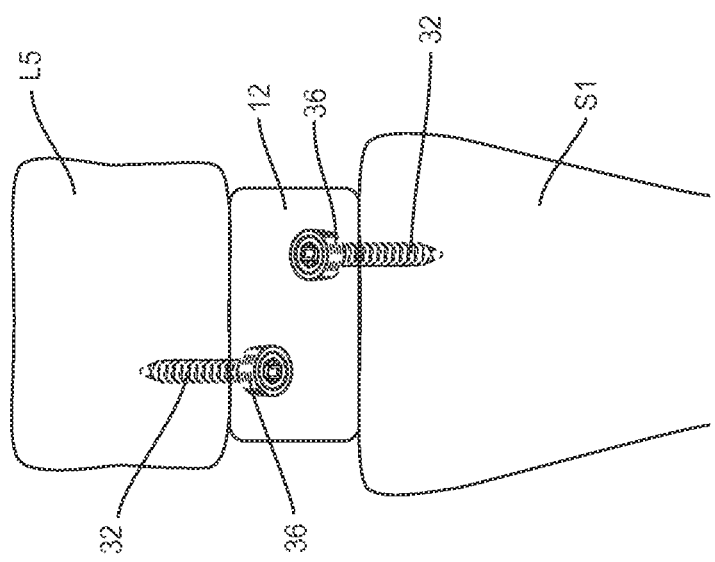
FIG. 9 is a plan view of components of one embodiment of a system in accordance with the principles of the present disclosure disposed with vertebrae.

In some embodiments, as shown for example in FIG. 10, spinal implant system 10 includes an interbody cage 12*a*, similar to interbody cage 12, which includes a surface that defines an opening configured to receive an agent, which may include bone graft (not shown) and/or other materials, as described herein, for employment in a fixation or fusion treatment. In some embodiments, the cross-sectional geometry of interbody cage 12*a* may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, interbody cage 12*a* includes one or more anterior windows 29*a*. In some embodiments, window 29*a* allows for additional packing of bone graft upon insertion of interbody cage 12*a* with tissue.

In some embodiments, bone screw 32 may be engaged with tissue in various orientations, such as, for example, series, parallel, offset, staggered and/or alternate vertebral levels. In some embodiments, one or more of bone screws 32 may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In assembly, operation and use, as shown in FIGS. 5-9, spinal implant system 10, similar to the systems described herein, is employed with a surgical procedure for treatment of a spinal disorder, such as those described herein, affecting a section of a spine of a patient. Spinal implant system 10 may also be employed with other surgical procedures. To treat the affected section of vertebrae V of a subject body of a patient, the patient is oriented such that the procedure can be performed anteriorly to provide direct anterior access to an L5-S1 intervertebral space along a surgical pathway, described herein, while avoiding selected muscular and abdominal anatomical structures. While some examples shown herein depict L5 and S1, it should be understood that the various embodiments could be used in procedures for the treatment of any selected levels of the human spine, including the cervical spine, thoracic spine and/or lumbar spine, including but not limited to disposing interbody cage 12*a*, similar to interbody cage 12 with screws 32, with the L4-L5 disc space, as shown in FIG. 10. In some embodiments, spinal implant system 10 is employed with a patient in a prone position, and/or employed with various additional surgical approaches to the spine, including posterior, posterior mid-line, direct lateral, postero-lateral, and/or antero lateral approaches.

In some embodiments, a discectomy is performed adjacent the L5-S1 intervertebral space. In some embodiments, sequential trial implants are delivered and used to distract the L5-S1 intervertebral space and apply appropriate tension in the L5-S1 intervertebral space allowing for indirect decompression. In some embodiments, the size of interbody cage 12 is selected after trialing, interbody cage 12 is visualized by fluoroscopy and oriented before malleting into the L5-S1 intervertebral space.

A preparation instrument is employed to remove disc tissue, fluids, adjacent tissues and/or bone, and scrape and/or remove tissue from endplate surfaces E1 of vertebra L5 and/or endplate surface E2 of vertebra S1. In some embodiments, vertebral facets, such as, for example, an L5 inferior facet and an S1 superior facet are resected. A trans-foraminal discectomy is performed to create vertebral space between vertebral bodies L5, S1.

In some embodiments, a resection of pedicles is conducted for further posterior compression to achieve a contact between the bony end plates and the superior and inferior portions of interbody cage 12. In some embodiments, the present surgical system is employed with a method that includes a transforaminal lumbar interbody fusion (TLIF) approach to provide a posterior discectomy and further posterior compression.

Interbody cage 12 is selected such that surface 18 is disposed at a selected angular orientation $\alpha$ relative to surface 20, as described herein. In some embodiments, pilot holes or the like are made in selected vertebra L5 and vertebra S1 of vertebrae V adjacent the L5-S1 intervertebral space for receiving bone screws 32. An inserter (not shown) is attached with interbody cage 12 to deliver interbody cage 12 adjacent to a surgical site for implantation adjacent the L5-S1 intervertebral space. Anterior surface 14 faces an anterior side of the body adjacent anterior portion A1 and posterior surface 16 faces a posterior side P1 of the body, as described herein. Surface 18 engages endplate tissue of endplate E1 and surface 20 is disposed facing endplate tissue of endplate E2.

Slot 30 is aligned with vertebra L5 and oriented to receive a bone screw 32/crown 36 assembly. In some embodiments, screw 32 and crown 36 are separately disposed with slot 30 and engaged therein. Crown 36 supports bone screw 32 and bone screw 32 slidably engages and/or translates relative to crown 36 and/or the surface that defines slot 30 in a first configuration, as described herein.

Bone screw 32 is engaged with tissue of vertebra L5. Bone screw 32 is movable and/or rotatable to one or a plurality of axial orientations in an angular range of $\beta 1$ relative to axis A2 and crown 36. Bone screw 32 abuts and/or frictionally engages crown 36 to resist and/or prevent backout of bone screw 32 from tissue of vertebra L5 and/or body 13.

Slot 40 is aligned with vertebra S1 and oriented to receive a bone screw 32/crown 36 assembly. In some embodiments, screw 32 and crown 36 are separately disposed with slot 40 and engaged therein. Crown 36 supports bone screw 32 and bone screw 32 slidably engages and/or translates relative to crown 36 and/or the surface that defines slot 40 in a first configuration, as described herein.

Bone screw 32 is engaged with tissue of vertebra S1. Bone screw 32 is movable and/or rotatable to one or a plurality of axial orientations in an angular range of $\beta 2$ relative to axis A3 and crown 36. Bone screw 32 abuts and/or frictionally engages crown 36 to resist and/or prevent backout of bone screw 32 from tissue of vertebra S1 and/or body 13.

Interbody cage 12 is disposed with vertebrae L5, S1 such that interbody cage 12 comprises a fulcrum between endplate surfaces E1, E2. Endplate surfaces E1, E2 engage surfaces 18, 20 to achieve a selected segmental lordosis of vertebrae L5, S1 as facilitated by angle $\alpha$. Endplate surfaces E1, E2 engage surfaces 18, 20 such that bone screw 32 abuts and/or frictionally engages crown 36 to lock screws 32 and interbody cage 12 in a fixed configuration with vertebrae L5, S1.

In some embodiments, spinal implant system 10 includes a surgical instrument I, as shown in FIGS. 6-9, employed to manipulate vertebrae L5, S1. Surgical instrument I includes lever arms, such as, for example, extender pedicles screws 70. Pedicle screws 70 are attached with vertebrae L5, S1 to manipulate vertebrae L5, S1. Surgical instrument I manipulates vertebrae L5, S1 such that endplate surfaces E1, E2 exert a compressive force, in the direction shown by arrows D in FIG. 7, on interbody cage 12 such that interbody cage 12 comprises a fulcrum during compression and screws 32 are movable to one or a plurality of axial orientations in a first configuration, as described herein. As such, surgical instrument I manipulates vertebrae L5, S1 to rotate vertebrae L5, S1, to achieve segmental lordosis of vertebrae L5, S1 as determined by angle α and locks screws 32 and interbody cage 12 in a fixed configuration with vertebrae L5, S1. In some embodiments, spinal implant system 10 includes interbody cage 12 employed in connection with a surgical procedure and method to treat a spine and facilitate manipulating vertebrae to a selected curvature and compression of a spine posteriorly without a complete PSO. For example, interbody cage 12 is employed with the surgical procedure and method, which includes a Smith-Petersen osteotomy for removal of only posterior-most bony structures of selected vertebral levels of vertebrae V, as described herein.

In some embodiments, spinal implant system 10 may comprise various surgical instruments, such as, for example, drivers, extenders, reducers, spreaders, distractors, blades, clamps, forceps, elevators and drills, which may be alternately sized and dimensioned, and arranged as a kit. In some embodiments, spinal implant system 10 may comprise the use of microsurgical and image guided technologies, such as, for example, surgical navigation components employing emitters and sensors, which may be employed to track introduction and/or delivery of the components of system 10 including the surgical instruments to a surgical site. See, for example, the surgical navigation components and their use as described in U.S. Pat. Nos. 6,021,343, 6,725,080 and 6,7969,88, the entire contents of each of these references being incorporated by reference herein.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies, as described herein, may be employed to access, view and repair spinal deterioration or damage, with the aid of spinal implant system 10. In some embodiments, spinal implant system 10 may include one or a plurality of interbody implants, rods, tethers, plates, connectors and/or bone fasteners for use with a single vertebral level or a plurality of vertebral levels. In some embodiments, spinal implant system 10 may include one or a plurality of bone fasteners that may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on, adjacent or about the components and/or surfaces of spinal implant system 10, and/or disposed with tissue. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Figure 11:
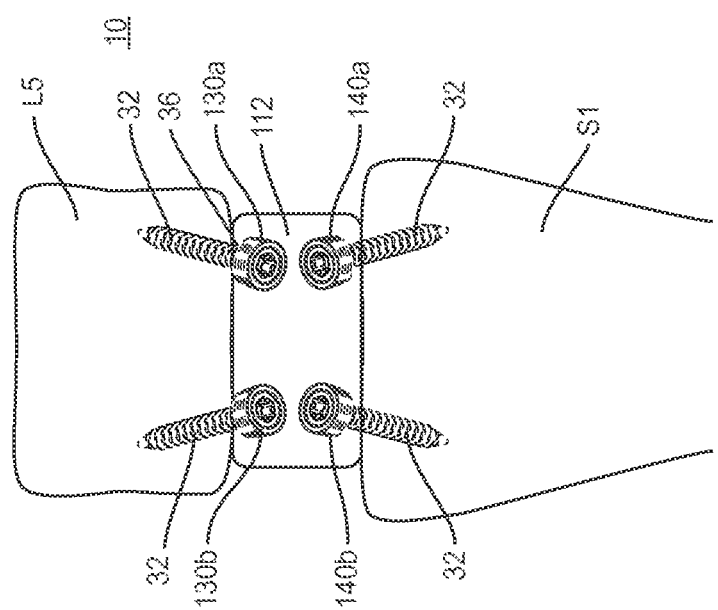
FIG. 11 is a plan view of components of one embodiment of a system in accordance with the principles of the present disclosure disposed with vertebrae.

In one embodiment, as shown in FIG. 11, spinal implant system 10, similar to the systems and methods described herein, comprises an interbody cage 112, similar to interbody cage 12 described herein. Interbody cage 112 includes a plurality of bone screws 32, as described herein, fastened with a first vertebral level, such as, for example, an L5 vertebral level and a plurality of bone screws 32 fastened with a second vertebral level, such as, for example, an S1 vertebral level.

Interbody cage 112 includes a plurality of spaced apart slots 130a, 130b, similar to slot 30 described herein, which are aligned with vertebra L5 and oriented to receive bone screw 32/crown 36 assemblies, similar to that described herein. Crown 36 supports bone screw 32 and bone screw 32 slidably engages and/or translates relative to crown 36 and/or the surfaces that define slots 130a, 130b in a first configuration, as described herein. Bone screws 32 disposed with slots 130a, 130b are engaged with tissue of vertebra L5 and rotatable to a plurality of axial orientations in a selected angular range relative to its axis and crown 36. Bone screws 32 abut and/or frictionally engage crowns 36 of slots 130a, 130b to resist and/or prevent backout of bone screws 32 from tissue of vertebra L5 and/or interbody cage 112.

Interbody cage 112 includes a plurality of spaced apart slots 140a, 140b, similar to slot 40 described herein, which are aligned with vertebra S1 and oriented to receive bone screw 32/crown 36 assemblies, similar to that described herein. Crown 36 supports bone screw 32 and bone screw 32 slidably engages and/or translates relative to crown 36 and/or the surfaces that define slots 140a, 140b in a first configuration, as described herein. Bone screws 32 disposed with slots 140a, 140b are engaged with tissue of vertebra S1 and rotatable to a plurality of axial orientations in a selected angular range relative to its axis and crown 36. Bone screws 32 abut and/or frictionally engage crowns 36 of slots 140a, 140b to resist and/or prevent backout of bone screws 32 from tissue of vertebra S1 and/or interbody cage 112.

Interbody cage 112 is disposed with vertebrae L5, S1 such that interbody cage 112 achieves a selected segmental lordosis of vertebrae L5, S1 similar to that described herein. The endplate surfaces of vertebrae L5, S1 engage the surfaces of interbody cage 112 such that bone screws 32 abut and/or frictionally engage crowns 36 of slots 130a, 130b, 140a, 140b to lock screws 32 and interbody cage 112 in a fixed configuration with vertebrae L5, S1.

Figure 12:
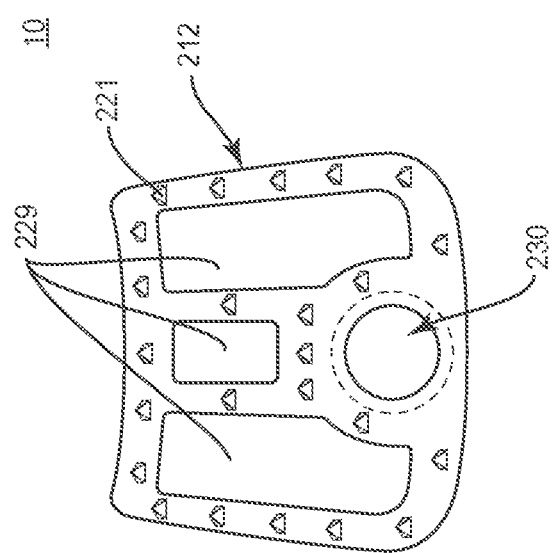
FIG. 12 is a side view of components of one embodiment of a system in accordance with the principles of the present disclosure.

In one embodiment, as shown in FIG. 12, spinal implant system 10, similar to the systems and methods described herein, comprises an interbody cage 212, similar to interbody cage 12 described herein. Interbody cage 212 includes a plurality of cavities, such as, for example, chambers 229 configured for disposal of an agent, as described herein. The outer surface of interbody cage 212 includes teeth 221, which may be oriented in one or a plurality of directions for engagement and fixation with tissue. In some embodiments, the outer surface of interbody cage 212 may be rough, textured, porous, semi-porous, dimpled, knurled, grooved and/or polished to facilitate engagement with tissue.

Interbody cage 212 defines an opening, such as, for example, a spheroidal joint 230. Spheroidal joint 230 is aligned with a selected vertebral level and oriented to receive a head 50 of a bone screw 32, as described herein. Spheroidal joint 230 supports head 50 and head 50 slidably engages the surfaces that define spheroidal joint 230 for relative movement therein in a first configuration, as described herein.

Bone screw 32 disposed with spheroidal joint 230 is engaged with tissue of a selected vertebral level and rotatable to a plurality of axial orientations in a selected angular range relative to its axis and spheroidal joint 230. Bone screw 32 abuts and/or frictionally engages the surfaces that define spheroidal joint 230 to resist and/or prevent backout of bone screw 32 from tissue of a selected vertebral level and/or interbody cage 212. Interbody cage 212 is disposed with selected vertebral levels such that interbody cage 212 achieves a selected segmental lordosis of the selected vertebral levels, similar to that described herein.

Figure 13:
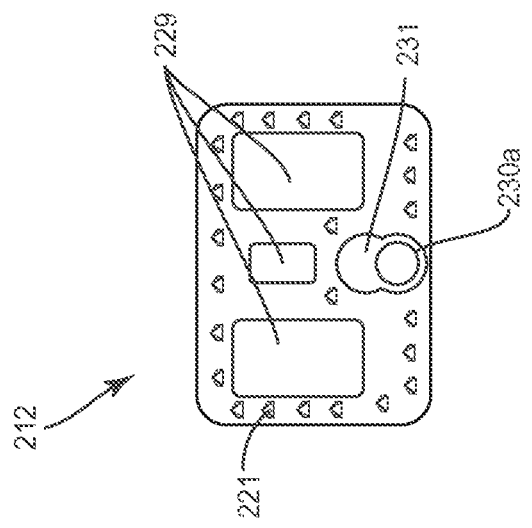
FIG. 13 is a side view of components of one embodiment of a system in accordance with the principles of the present disclosure.

The endplate surfaces of the selected vertebral levels engage the surfaces of interbody cage 212 such that bone screw 32 abuts and/or frictionally engages the surfaces that define spheroidal joint 230 to lock screw 32 and interbody cage 212 in a fixed configuration with the selected vertebral levels. In some embodiments, interbody cage 212 can include one or a plurality of spheroidal joints 230, which may be aligned, co-axial, define a trajectory, arcuately oriented, offset, staggered, in series, parallel, transverse and/or spaced apart. In some embodiments, as shown in FIG. 13, interbody cage 212 includes a spheroidal joint 230a having an extended chamber 231 with an increase in posterior translation and/or mobility of head 50 to facilitate posterior translation and/or mobility of screw 32.

Figure 15:
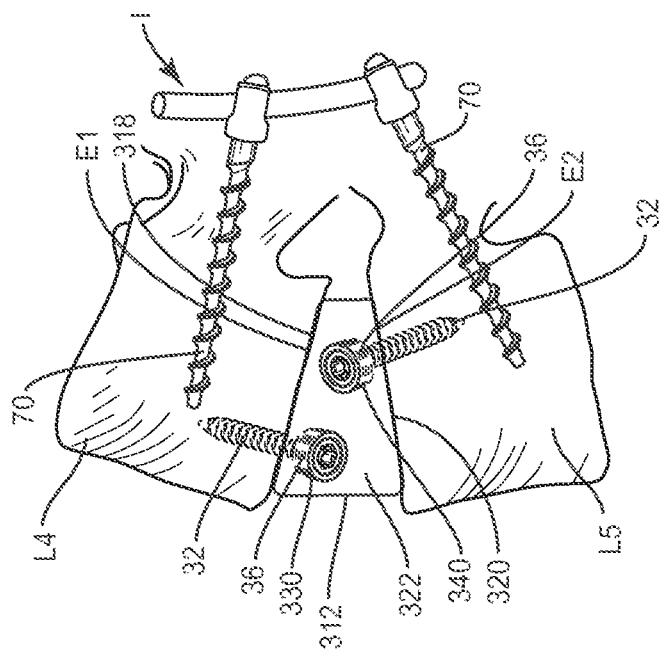
FIG. 15 is a side view of components of one embodiment of a system in accordance with the principles of the present disclosure disposed with vertebrae.
Figure 14:
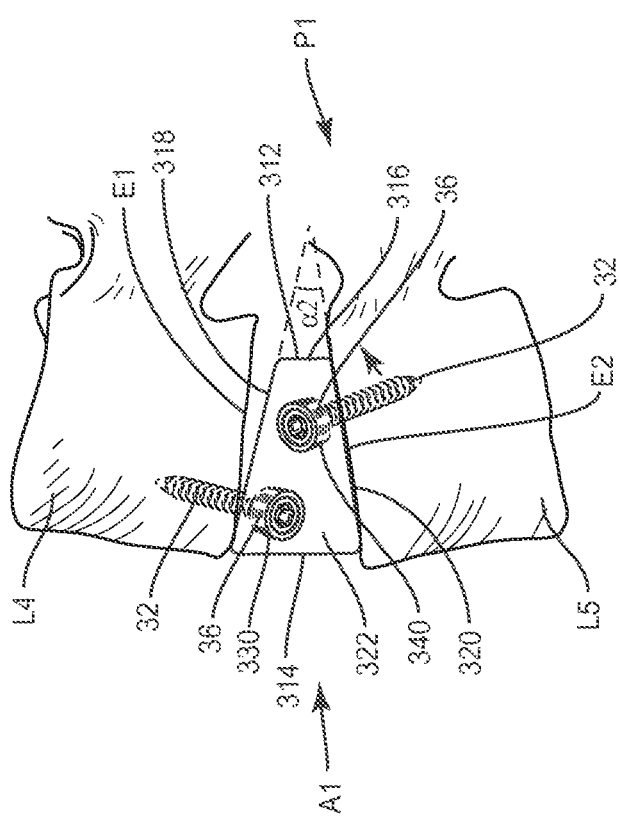
FIG. 14 is a side view of components of one embodiment of a system in accordance with the principles of the present disclosure disposed with vertebrae.
Figure 16:
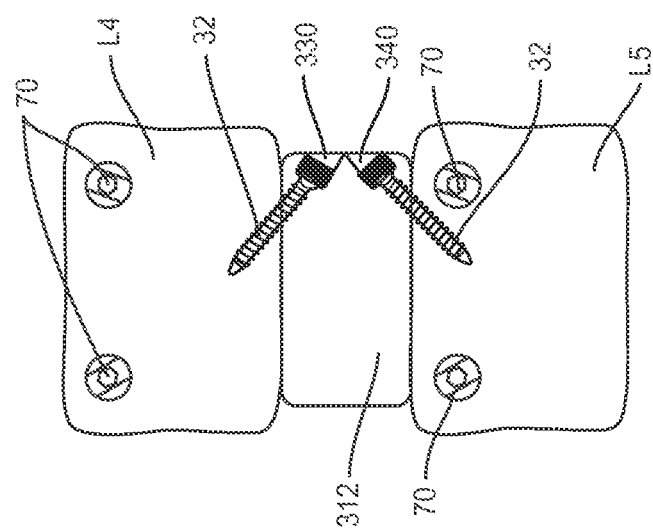
FIG. 16 is a side view of components of one embodiment of a system in accordance with the principles of the present disclosure disposed with vertebrae.

In one embodiment, as shown in FIGS. 14-16, spinal implant system 10, similar to the systems and methods described herein, comprises an interbody cage 312, similar to interbody cage 12 described herein. Interbody cage 312 is configured for implantation along a direct lateral interbody fusion (DLIF) approach.

Interbody cage 312 is selected and the components of interbody cage 312 are delivered via a lateral surgical pathway to the surgical site such that a surface 318 is disposed at a selected angular orientation $\alpha 2$ relative to a surface 320, similar to that described herein. Pilot holes or the like are made in selected vertebra L4 and vertebra L5 of vertebrae adjacent the L4-L5 intervertebral space for receiving bone screws 32. An inserter (not shown) is attached with interbody cage 312 to deliver interbody cage 312 adjacent to a surgical site for implantation adjacent the L4-L5 intervertebral space. Anterior surface 314 faces an anterior side of the body adjacent anterior portion A1 and posterior surface 316 faces a posterior side P1 of the body, as described herein. Surface 318 engages endplate tissue of endplate E1 and surface 320 is disposed facing endplate tissue of endplate E2.

A slot 330, similar to slot 30 described herein, is aligned with vertebra L4 and oriented to receive a bone screw 32/crown 36 assembly, similar to that described herein. Crown 36 supports bone screw 32 and bone screw 32 slidably engages and/or translates relative to crown 36 and/or the surface that defines slot 330 in a first configuration, as described herein.

Bone screw 32 is engaged with tissue of vertebra L4. Bone screw 32 is movable and/or rotatable to one or a plurality of axial orientations in a selected angular range relative to its axis and crown 36, similar to that described herein. Bone screw 32 abuts and/or frictionally engages crown 36 to resist and/or prevent backout of bone screw 32 from tissue of vertebra L4 and/or interbody cage 312.

A slot 340, similar to slot 40 described herein, is aligned with vertebra L5 and oriented to receive a bone screw 32/crown 36 assembly, similar to that described herein. Crown 36 supports bone screw 32 and bone screw 32 slidably engages and/or translates relative to crown 36 and/or the surface that defines slot 340 in a first configuration, as described herein.

Bone screw 32 is engaged with tissue of vertebra L5. Bone screw 32 is movable and/or rotatable to one or a plurality of axial orientations in a selected angular range relative to its axis and crown 36. Bone screw 32 abuts and/or frictionally engages crown 36 to resist and/or prevent backout of bone screw 32 from tissue of vertebra L5 and/or interbody cage 312.

Interbody cage 312 is disposed with vertebrae L4, L5 such that interbody cage 312 comprises a fulcrum between endplate surfaces E1, E2. Endplate surfaces E1, E2 engage surfaces 318, 320 to achieve a selected segmental lordosis of vertebrae L4, L5 as facilitated by angle $\alpha 2$. Endplate surfaces E1, E2 engage surfaces 318, 320 such that bone screw 32 abuts and/or frictionally engages crown 36 to lock screws 32 and interbody cage 312 in a fixed configuration with vertebrae L4, L5.

In some embodiments, spinal implant system 10 includes a surgical instrument I, as shown in FIGS. 15 and 16, employed to manipulate vertebrae L4, L5. Surgical instrument I includes extender pedicles screws 70, which are attached with vertebrae L4, L5 to manipulate vertebrae L4, L5. Surgical instrument I manipulates vertebrae L4, L5 such that endplate surfaces E1, E2 exert a compressive force on interbody cage 312 such that interbody cage 312 comprises a fulcrum during compression and screws 32 are movable to one or a plurality of axial orientations in a first configuration, as described herein. As such, surgical instrument I manipulates vertebrae L4, L5 to rotate vertebrae L4, L5, to achieve segmental lordosis of vertebrae L4, L5 as determined by angle $\alpha 2$ and locks screws 32 and interbody cage 312 in a fixed configuration with vertebrae L4, L5.

Figure 17:
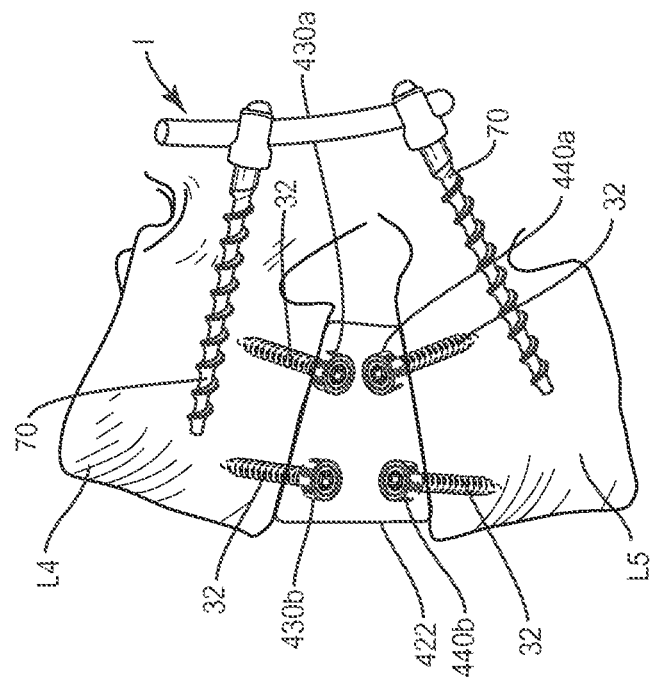
FIG. 17 is a side view of components of one embodiment of a system in accordance with the principles of the present disclosure disposed with vertebrae.

In one embodiment, as shown in FIG. 17, spinal implant system 10, similar to the systems and methods described herein, comprises an interbody cage 412, similar to interbody cage 312 described herein. The components of interbody cage 412 are delivered via a lateral surgical pathway to the surgical site and include a plurality of bone screws 32, as described herein, fastened with an L4 vertebral level and a plurality of bone screws 32 fastened with an L5 vertebral level.

Interbody cage 412 includes a plurality of spaced apart slots 430a, 430b, similar to slot 330 described herein, which are aligned with vertebra L4 and oriented to receive bone screw 32/crown 36 assemblies, similar to that described herein. Crown 36 supports bone screw 32 and bone screw 32 slidably engages and/or translates relative to crown 36 and/or the surfaces that define slots 430a, 430b in a first configuration, as described herein. Bone screws 32 disposed with slots 430a, 430b are engaged with tissue of vertebra L4 and rotatable to a plurality of axial orientations in a selected angular range relative to its axis and crown 36. Bone screws 32 abut and/or frictionally engage crowns 36 of slots 430a, 430b to resist and/or prevent backout of bone screws 32 from tissue of vertebra L4 and/or interbody cage 412.

Interbody cage 412 includes a plurality of spaced apart slots 440a, 440b, similar to slot 340 described herein, which are aligned with vertebra L5 and oriented to receive bone screw 32/crown 36 assemblies, similar to that described herein. Crown 36 supports bone screw 32 and bone screw 32 slidably engages and/or translates relative to crown 36 and/or the surfaces that define slots 440a, 440b in a first configuration, as described herein. Bone screws 32 disposed with slots 440a, 440b are engaged with tissue of vertebra L5 and rotatable to a plurality of axial orientations in a selected angular range relative to its axis and crown 36. Bone screws 32 abut and/or frictionally engage crowns 36 of slots 440a, 440b to resist and/or prevent backout of bone screws 32 from tissue of vertebra L5 and/or interbody cage 412.

A surgical instrument I manipulates vertebrae L4, L5. Surgical instrument I includes extender pedicles screws 70, which are attached with vertebrae L4, L5 to manipulate vertebrae L4, L5. Surgical instrument I manipulates vertebrae L4, L5 such that endplate surfaces of vertebrae L4, L5 exert a compressive force on interbody cage 412 such that interbody cage 412 comprises a fulcrum during compression and screws 32 are movable to one or a plurality of axial orientations in a first configuration, as described herein. As such, surgical instrument I manipulates vertebrae L4, L5 to rotate vertebrae L4, L5, to achieve segmental lordosis of vertebrae L4, L5 and locks screws 32 and interbody cage 412 in a fixed configuration with vertebrae L4, L5.

In one embodiment, as shown in FIGS. 18-22, spinal implant system 10, similar to the systems and methods described herein, comprises an interbody cage 512, similar to the interbody cages described herein. Interbody cage 512 extends between an anterior surface 514 and a posterior surface 516. Anterior surface 514 is configured to face an anterior side of a body and be disposed adjacent to an anterior portion of vertebrae, such as, for example, an anterior portion of a cervical spine and intervertebral space between a C2 vertebra and a C3 vertebra of vertebrae V. Posterior surface 516 is configured to face a posterior side of a patient body and be disposed adjacent a posterior portion of vertebrae, such as, for example, a posterior portion of the C2-C3 intervertebral space.

Interbody cage 512 includes a surface 518 disposed at a selected angular orientation relative to a surface 520, similar to surfaces 18, 20 described herein, to form interbody cage 512 for achieving segmental lordosis of one or more vertebra adjacent the C2-C3 intervertebral space, similar to that described herein.

Interbody cage 512 is selected such that surface 518 is disposed at a selected angular orientation relative to surface 520, similar to that described herein. Pilot holes or the like are made in selected vertebra C2 and vertebra C3 of vertebrae adjacent the C2-C3 intervertebral space for receiving bone screws 32. An inserter (not shown) is attached with interbody cage 512 to deliver interbody cage 512 adjacent to a surgical site for implantation adjacent the C2-C3 intervertebral space. Surface 518 engages endplate tissue of vertebra C2 and surface 320 is disposed facing endplate tissue of vertebra C3.

A slot 530, similar to slot 30 described herein, is aligned with vertebra C2 and oriented to receive a bone screw 32/crown 36 assembly, similar to that described herein. Crown 36 supports bone screw 32 and bone screw 32 slidably engages and/or translates relative to crown 36 and/or the surface that defines slot 530 in a first configuration, as described herein. Bone screw 32 is engaged with tissue of vertebra C2. Bone screw 32 is movable and/or rotatable to one or a plurality of axial orientations in a selected angular range relative to its axis and crown 36, similar to that described herein. Bone screw 32 abuts and/or frictionally engages crown 36 to resist and/or prevent backout of bone screw 32 from tissue of vertebra C2 and/or interbody cage 512.

A slot 540, similar to slot 40 described herein, is aligned with vertebra C3 and oriented to receive a bone screw 32/crown 36 assembly, similar to that described herein. Crown 36 supports bone screw 32 and bone screw 32 slidably engages and/or translates relative to crown 36 and/or the surface that defines slot 540 in a first configuration, as described herein. Bone screw 32 is engaged with tissue of vertebra C3. Bone screw 32 is movable and/or rotatable to one or a plurality of axial orientations in a selected angular range relative to its axis and crown 36. Bone screw 32 abuts and/or frictionally engages crown 36 to resist and/or prevent backout of bone screw 32 from tissue of vertebra C3 and/or interbody cage 512.

Figure 23:
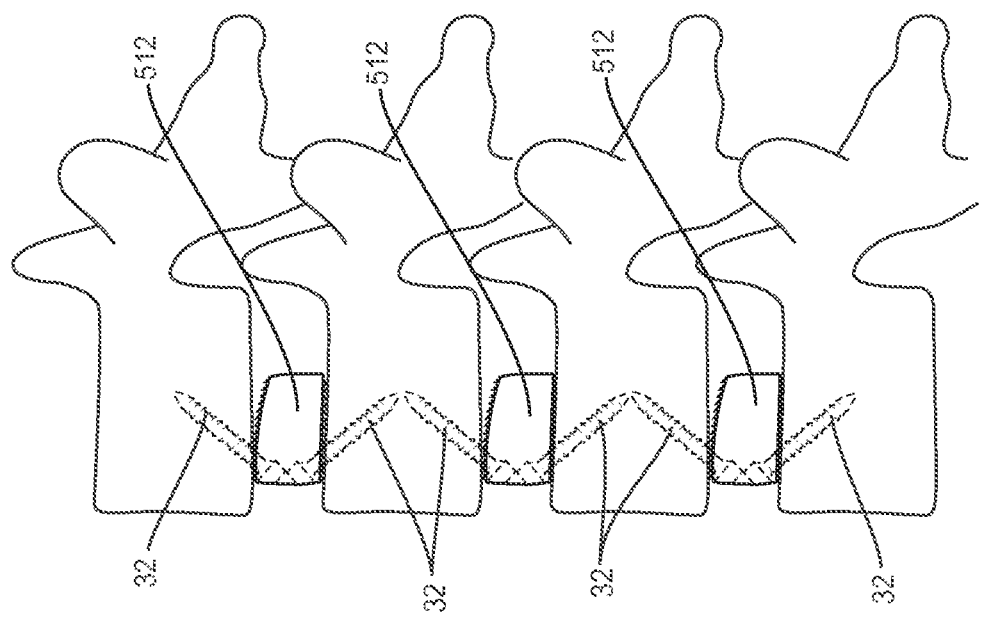
FIG. 23 is a side view of components of one embodiment of a system in accordance with the principles of the present disclosure disposed with vertebrae.

Interbody cage 512 is disposed with vertebrae C2, C3 such that interbody cage 512 comprises a fulcrum between the endplate surfaces of vertebrae C2, C3. The endplate surfaces engage surfaces 518, 520 to achieve a selected segmental lordosis of vertebrae C2, C3. In some embodiments, the endplate surfaces engage surfaces 518, 520 such that bone screw 32 abuts and/or frictionally engages crown 36 to lock screws 32 and interbody cage 512 in a fixed configuration with vertebrae C2, C3. In some embodiments, as shown in FIG. 23, spinal implant system 10 includes a plurality of interbody cages 512 implanted with a plurality of intervertebral spaces between a plurality of vertebral levels of the cervical spine to treat a cervical kyphotic deformity with stand-alone instrumentation such that a kyphotic cervical spine is corrected to a selected lordotic cervical spine, as described herein.

Figure 18:
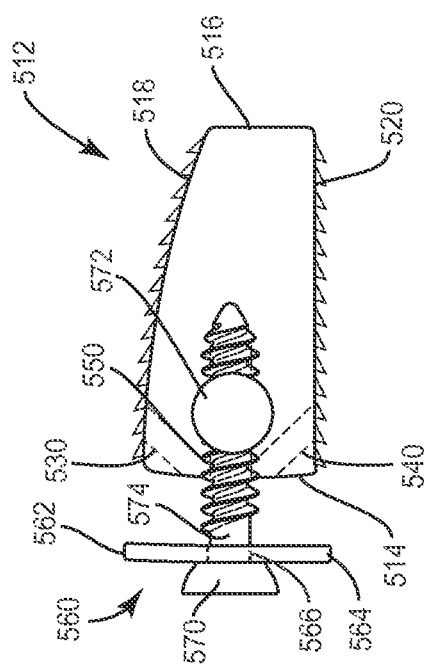
FIG. 18 is a side view of components of one embodiment of a system in accordance with the principles of the present disclosure.

In some embodiments, interbody cage 512 defines an opening, such as, for example, a spheroidal joint 550, as shown in FIG. 18. Spheroidal joint 550 is oriented to receive a head 572 of a step bolt screw 570. Spheroidal joint 550 supports head 572 and head 572 slidably engages the surfaces that define spheroidal joint 550 for relative movement therein in a first configuration, as described herein.

Figure 19:
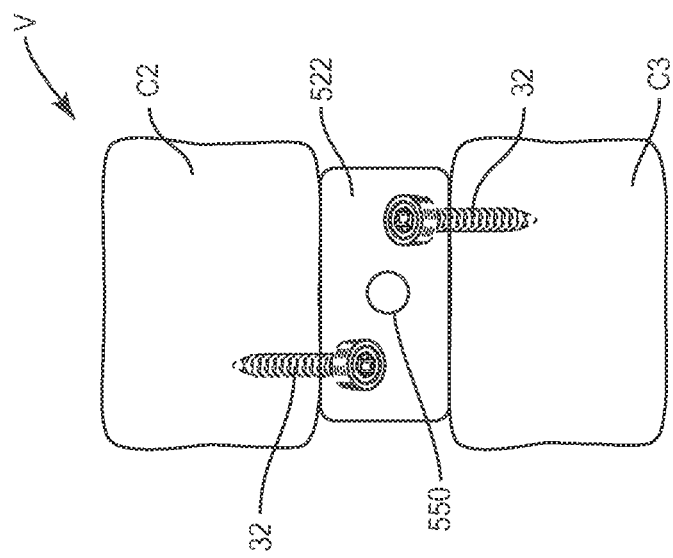
FIG. 19 is a plan view of components of one embodiment of a system in accordance with the principles of the present disclosure disposed with vertebrae.

Step bolt screw 570 disposed with spheroidal joint 550 is rotatable to a plurality of axial orientations in a selected angular range relative to its axis and spheroidal joint 550. In some embodiments, step bolt screw 570 abuts and/or frictionally engages the surfaces that define spheroidal joint 550 to resist and/or prevent backout of step bolt screw 570 from interbody cage 512. In some embodiments, step bolt screw 570 abuts and/or frictionally engages the surfaces that define spheroidal joint 550 to lock step bolt screw 570 and interbody cage 512 in a fixed configuration with vertebrae C2, C3. In some embodiments, interbody cage 512 can include one or a plurality of spheroidal joints 550, which may be aligned, co-axial, define a trajectory, arcuately oriented, offset, staggered, in series, parallel, transverse and/or spaced apart. Spheroidal joint 550 is disposed centrally between slot 530 and slot 540, as shown in FIG. 19.

Figure 20:
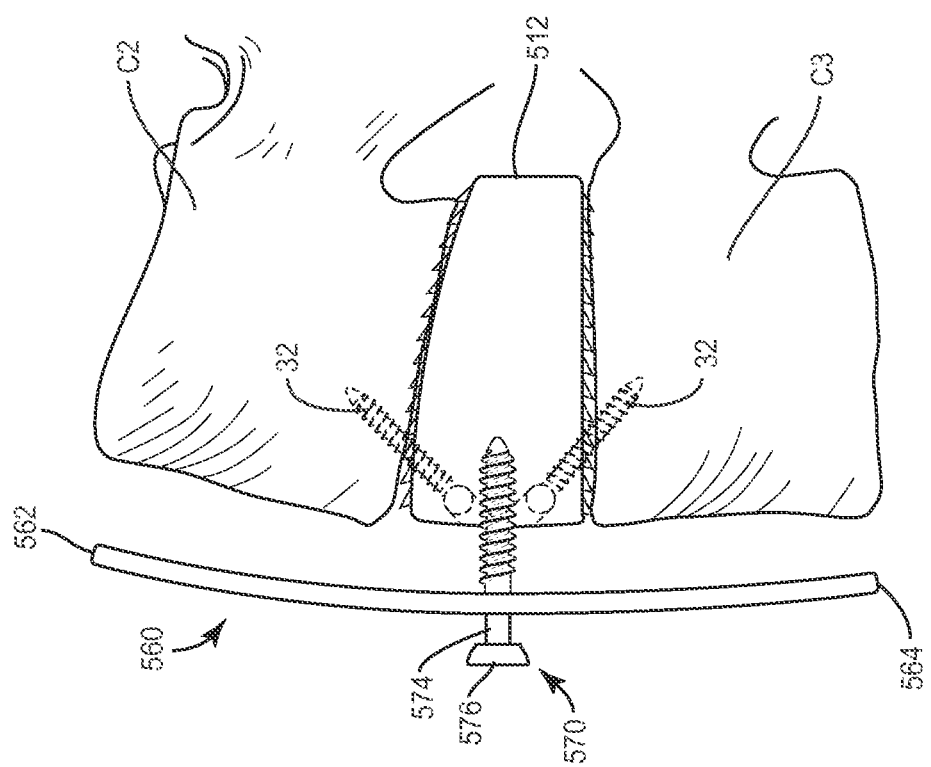
FIG. 20 is a side view of components of one embodiment of a system in accordance with the principles of the present disclosure disposed with vertebrae.
Figure 22:
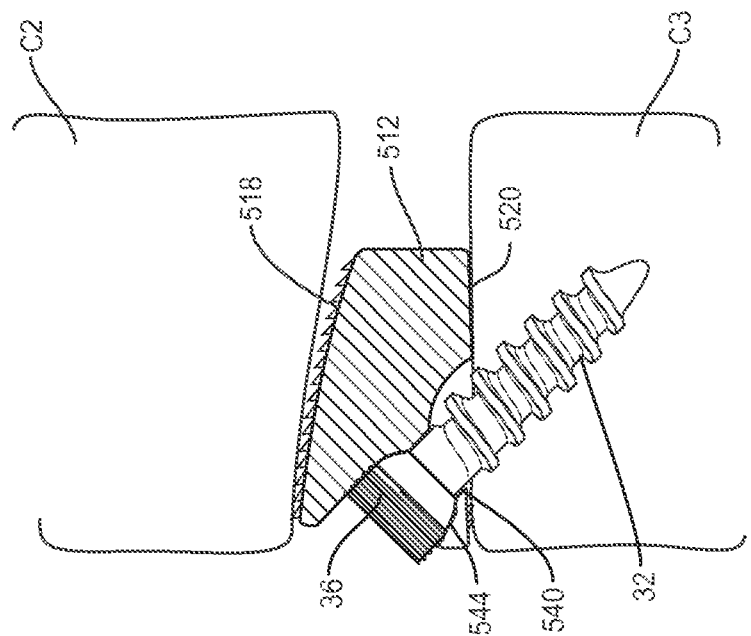
FIG. 22 is a para-sagittal cross section view of components of one embodiment of a system in accordance with the principles of the present disclosure disposed with vertebrae.
Figure 21:
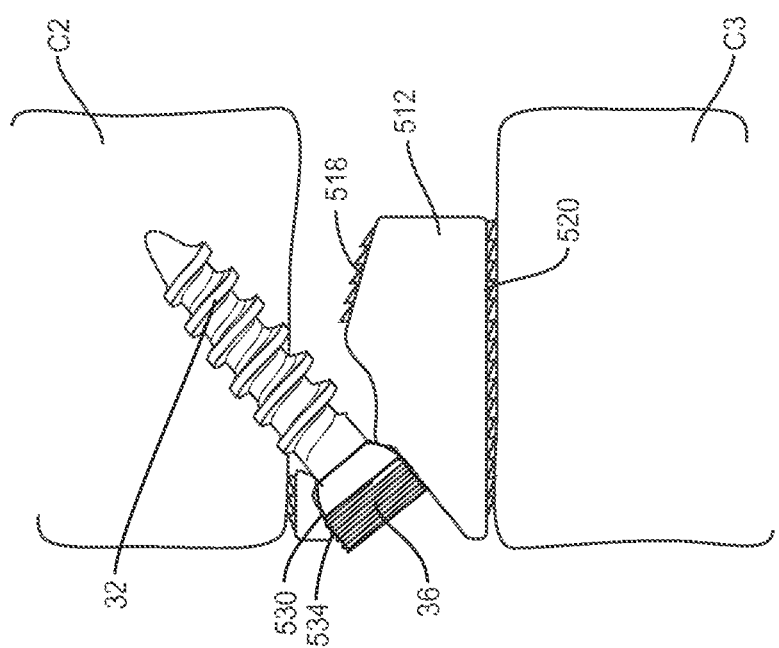
FIG. 21 is a para-sagittal cross section view of components of one embodiment of a system in accordance with the principles of the present disclosure disposed with vertebrae.

Interbody cage 512 includes a plate 560, which has a substantially rectangular configuration. In some embodiments, plate 560 can be variously configured, such as, for example, tubular, oval, oblong, triangular, square, polygonal, irregular, uniform, non-uniform, variable, hollow and/or tapered. Plate 560 includes a portion 562 configured to engage a vertebral level, such as, for example, vertebra C2 and a portion 564 configured to engage a vertebral level, such as, for example, vertebra C3, as shown in FIG. 20. In one embodiment, plate 560 may be attached with interbody cage 512 prior to implantation or in situ.

Figure 24:
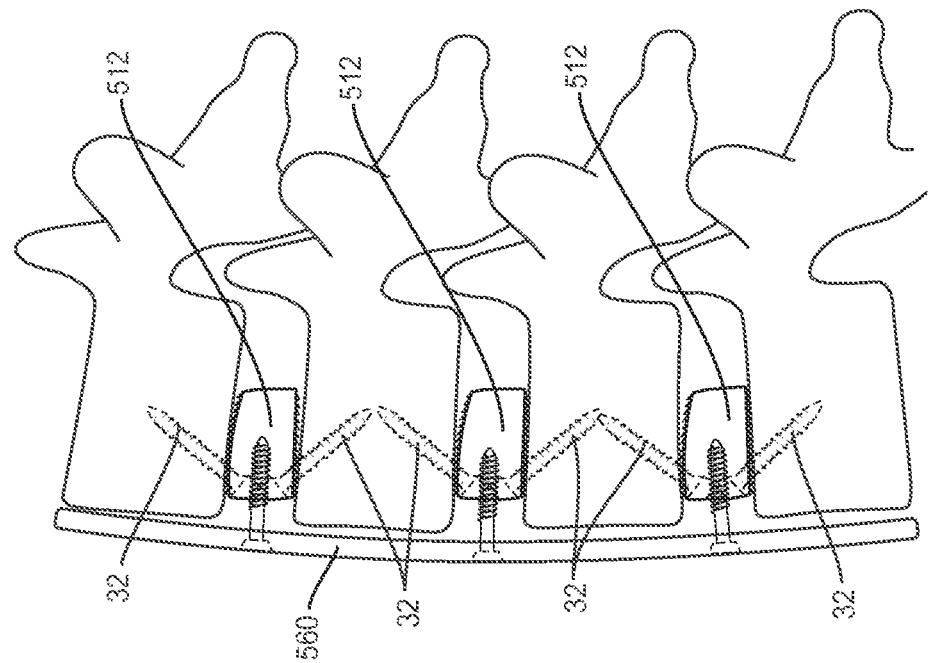
FIG. 24 is a side view of components of one embodiment of a system in accordance with the principles of the present disclosure disposed with vertebrae.

Plate 560 includes an opening 566 configured for disposal of step bolt screw 570 to connect plate 560 with interbody cage 512. Step bolt screw 570 includes an elongated post 574 configured for disposal with opening 566. Plate 560 is configured for translation and angulation along post 574 to facilitate orientation and engagement of plate 560 with vertebrae for fixing the components of interbody cage 512 with vertebrae. A nut 576 is threaded with step bolt screw 570 to lock plate 560 with interbody cage 512 to fix the components of interbody cage 512 with vertebrae. In some embodiments, as shown in FIG. 24, spinal implant system 10 includes a plurality of interbody cages 512 and a plate 560 that extends over a plurality of vertebral levels. Interbody cages 512 are implanted with a plurality of intervertebral spaces between a plurality of vertebral levels of the cervical spine and plate 560 is connected with the plurality of vertebral levels to treat a cervical kyphotic deformity with stand-alone instrumentation such that a kyphotic cervical spine is corrected to a selected lordotic cervical spine, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
    a body including a first vertebral engaging surface and a second vertebral engaging surface, the first vertebral engaging surface being disposed relative to the second vertebral engaging surface at a selected angular orientation, the body defining a first opening that extends through the first vertebral engaging surface and a second opening that extends through the second vertebral engaging surface;
    a first crown comprising a threaded outer surface that engages a threaded portion of the first opening and a first inner surface that defines a first cavity;
    a second crown comprising a threaded outer surface that engages a threaded portion of the second opening and a second inner surface that defines a second cavity;
    a first fastener extending along a first longitudinal axis between a first shaft and a first head, the first fastener being disposed with the first opening such that the first head is positioned within the first cavity and the first inner surface intersects the first longitudinal axis; and
    a second fastener extending along a second longitudinal axis between a second shaft and a second head, the second fastener being disposed with the second opening such that the second head is positioned within the second cavity and the second inner surface intersects the second longitudinal axis, the fasteners being engageable with the body between a first configuration such that the fasteners are each movable to a plurality of axial orientations relative to the body and a second configuration such that the fasteners are each fixed relative to the body, the crowns preventing the fasteners from translating in a linear direction relative to the body when the fasteners are in the first and second configurations.

2. A spinal implant as recited in claim 1, wherein the fasteners are engaged with the body to resist and/or prevent backout of the fasteners from vertebral tissue.

3. A spinal implant as recited in claim 1, wherein the heads are spherical and are rotatable within the openings in the first configuration.

4. A spinal implant as recited in claim 1, wherein the openings each comprise an axial slot.

5. A spinal implant as recited in claim 4, wherein the body includes spaced apart inner surfaces that define the axial slots, the inner surfaces of the body engaging the fasteners to resist and/or prevent backout of the fasteners from vertebral tissue.

6. A spinal implant as recited in claim 1, wherein the crowns are disposed with the openings and configured to support the fasteners.

7. A spinal implant as recited in claim 1, wherein the openings each define a crown axis and the fasteners are movable to the plurality of axial orientations in a range of 0 through 25 degrees relative to the crown axes.

8. A spinal implant as recited in claim 1, further comprising an anterior plate connected to the body.

9. A spinal implant as recited in claim 8, wherein the plate is connected to the body via a screw that is engageable with the plate and fixed with the body between a first configuration such that the screw is movable to a plurality of axial orientations relative to the body and a second configuration such that the screw is fixed relative to the body.

10. A spinal implant as recited in claim 1, wherein the cavities are semi-spherical.

11. A spinal implant as recited in claim 1, wherein the cavities and the heads are each semi-spherical.

12. A spinal implant as recited in claim 1, wherein the inner surfaces are smooth to facilitate rotation of the heads within the crowns within a plurality of axial orientations.

13. A spinal implant as recited in claim 1, wherein the inner surfaces each define a circumferential flange that is configured to retain one of the heads and facilitate rotation of one of the fasteners.

14. A spinal implant as recited in claim 1, wherein the inner surfaces engage the heads for a friction fit between the inner surfaces and the heads to fix the fasteners relative to the body.

15. A spinal implant as recited in claim 1, wherein the selected angular orientation is an angle in a range of −2 through 26 degrees.

16. A spinal implant as recited in claim 1, wherein the selected angular orientation is an angle in a range of 4 through −14 degrees.

17. A spinal implant as recited in claim 1, wherein the selected angular orientation is a 40 degree angle.

18. A spinal implant as recited in claim 1, wherein the body comprises a wall that extends from the first vertebral engaging surface to the second vertebral engaging surface, the openings each extending through the wall, the crowns each comprising an outer surface that is flush with an outer surface of the wall.

19. An interbody cage comprising:
    a body extending between an anterior surface and a posterior surface, and including a first vertebral engaging surface and a second vertebral engaging surface, the first vertebral engaging surface being disposed relative to the second vertebral engaging surface at a selected angular orientation for achieving segmental lordosis of one or more vertebra, the body defining a first opening configured to be disposed in alignment with a first vertebral surface and a second opening configured to be disposed in alignment with a second vertebral surface, the vertebral surfaces defining an intervertebral disc space;
    a first crown comprising a threaded outer surface that engages a threaded portion of the first opening and a first inner surface that defines a first cavity;
    a second crown comprising a threaded outer surface that engages a threaded portion of the second opening and a second inner surface that defines a second cavity;
    a first multi-axial bone screw extending along a first longitudinal axis between a first head and a first threaded shaft configured for fixation with the first vertebral surface, the first screw being disposed with the first opening such that the first head is positioned within the first cavity and the first inner surface intersects the first longitudinal axis; and a second multi-axial bone screw including a second head disposed with the second opening and a second threaded shaft configured for fixation with the second vertebral surface, the second screw being disposed with the second opening such that the second head is positioned within the second cavity and the second inner surface intersects the second longitudinal axis, each of the screws being engageable with the body between a first configuration such that the screws are movable to a plurality of axial orientations relative to the body and a second configuration such that the screws are fixed relative to the body, the crowns preventing the screws from translating in a linear direction relative to the body when the screws are in the first and second configurations.

20. A spinal implant comprising:

a body including a first vertebral engaging surface and a second vertebral engaging surface, the first vertebral engaging surface being disposed relative to the second vertebral engaging surface at a selected angular orientation, the body comprising a wall that extends between the vertebral engaging surfaces, the body defining a first opening that extends through the wall and the first vertebral engaging surface and a second opening that extends through the wall and the second vertebral engaging surface;

a first crown comprising a threaded outer surface that engages a threaded portion of the first opening and a smooth first inner surface that defines a semi-spherical first cavity;

a second crown comprising a threaded outer surface that engages a threaded portion of the second opening and a smooth second inner surface that defines a semi-spherical second cavity;

a first fastener extending along a first longitudinal axis between a first shaft and a semi-spherical first head, the first fastener being disposed with the first opening such that the first head is positioned within the first cavity and the first inner surface intersects the first longitudinal axis; and a second fastener extending along a second longitudinal axis between a second shaft and a semi-spherical second head, the second fastener being disposed with the second opening such that the second head is positioned within the first cavity and the second inner surface intersects the second longitudinal axis, the fasteners each being engageable with the body between a first configuration in which the fasteners are movable to a plurality of axial orientations relative to the body and a second configuration in which the fasteners are fixed relative to the body, the crowns preventing the fasteners from translating in a linear direction relative to the body when the fasteners are in the first and second configurations, wherein the inner surface defines a circumferential flange that is configured to retain the head and facilitate rotation of the at least one fastener.

* * * * *

UNITED STATES PATENT AND TRADEMARK OFFICE
CERTIFICATE OF CORRECTION

PATENT NO.        : 9,901,461 B2                               Page 1 of 1
APPLICATION NO.   : 14/692463
DATED             : February 27, 2018
INVENTOR(S)       : Arlet It is certified that error appears in the above-identified patent and that said Letters Patent is hereby corrected as shown below:

In the Specification

In Column 6, Line 24, delete "L4/5" and insert -- L4/L5 --, therefor.

In Column 9, Line 27, delete "(e.g., SKELITE)," and insert -- (e.g., SKELITE™), --, therefor.

Signed and Sealed this
Seventeenth Day of July, 2018

Andrei Iancu
*Director of the United States Patent and Trademark Office*